United States Patent [19]

Knifton et al.

[11] Patent Number: 4,898,995

[45] Date of Patent: Feb. 6, 1990

[54] METHOD FOR PRODUCTION OF PHENOL/ACETONE FROM CUMENE HYDROPEROXIDE

[75] Inventors: John F. Knifton, Austin; John R. Sanderson, Leander, both of Tex.

[73] Assignee: Texaco Chemical Company, White Plains, N.Y.

[21] Appl. No.: 261,817

[22] Filed: Oct. 24, 1988

[51] Int. Cl.$^4$ .................. C07C 37/08; C07C 45/53
[52] U.S. Cl. .................. 568/798; 568/485; 568/741; 568/768
[58] Field of Search ............... 568/485, 741, 798, 768

[56] References Cited

U.S. PATENT DOCUMENTS

| | | | |
|---|---|---|---|
| 2,628,983 | 2/1953 | Aller | 568/798 |
| 2,628,984 | 2/1953 | Aller | 568/798 |
| 2,715,145 | 8/1955 | Bewley et al. | 568/798 |
| 2,889,368 | 6/1959 | Hiratsuka et al. | 568/798 |
| 4,209,465 | 6/1980 | Austin et al. | 568/798 |
| 4,246,203 | 1/1981 | Wirth | 568/798 |
| 4,267,379 | 5/1981 | Austin | 568/798 |
| 4,267,380 | 5/1981 | Austin | 568/798 |
| 4,482,757 | 11/1984 | Drake | 568/798 |

FOREIGN PATENT DOCUMENTS

| | | | |
|---|---|---|---|
| 0157531 | 12/1979 | Japan | 568/798 |
| 0992508 | 1/1983 | U.S.S.R. | 568/798 |

*Primary Examiner*—Werren B. Lone
*Attorney, Agent, or Firm*—Jack H. Park; Kenneth R. Priem; Cynthia L. Kendrick

[57] ABSTRACT

A method is disclosed for the synthesis of phenol and acetone by decomposition over a heterogeneous catalyst from the group consisting of a heteropoly acid on an inert support or an ion exchange resin with a sulfonic acid functionality. The method allows for quantitative conversions with yields of up to >99 mole % or better.

15 Claims, No Drawings

METHOD FOR PRODUCTION OF PHENOL/ACETONE FROM CUMENE HYDROPEROXIDE

CROSS-REFERENCE

This application is related to U.S. patent application Ser. Nos. 261,818, and 261,819.

This invention relates to novel methods for the decomposition of organic hydroperoxides, and more particularly this invention relates to a method for producing phenol and acetone by decomposition of cumene hydroperoxide over two types of heterogeneous catalyst. In the first embodiment heterogeneous catalysts comprise heteropoly acids, such as tungstophosphoric, molybdophosphoric, tungstosilicic and molybdosilicic, supported on titania. Another embodiment comprises the use of particular ion exchange resins having a sulfonic acid functionality. The invention is particularly advantageous in that there is quantitative conversion of cumene hydroperoxide under mild conditions. The catalyst is very attractive in that analysis shows by-products are produced in much smaller percentages than with standard acid catalysis.

BACKGROUND OF THE INVENTION

It is known to those skilled in the art that cumene can be oxidized to cumene hydroperoxide and that cumene hydroperoxide can be decomposed by various means to provide phenol and acetone.

In U.S. Pat. No. 2,889,368 to Hiratsuka there is a process discussed for the decomposition of various organic hydroperoxide substances, such as, for example, cumene hydroperoxide. The cumene hydroperoxide is decomposed in the presence of a 10 to 70% aqueous sulfuric acid solution at a temperature between about 50° and 100° C. to phenol and acetone, the yields amounting to 80-90%.

Today, the disadvantages of using soluble strong acid catalysts in this application include (a) the need for an efficient means of separating the phenol/acetone products from the acid or spent acid catalyst, (b) the need to neutralize said acids with caustic etc., (c) the disposal of salts generated as a result of said neutralization, and (d) the difficulty in obtaining >99.9% purity phenol from such a process if there is any entrainment or contamination of the crude phenol/acetone product by said acid catalyst.

U.S. Pat. No. 2,715.145 concerns a process for increasing the yield of phenol by decomposing the material contained in the peroxide acidic catalyst decomposition mixture. Again it is disclosed that the decomposition can be promoted by the addition to the residue of acids such as sulfuric acid, phosphoric acid or sulfonic acids, as well as acid washed activated earth, such as Fuller's earth.

A decomposition catalyst of sulfur dioxide or sulfuric acid is also used in U.S. Pat. No. 4,016,213 to obtain phenol and acetone from cumene hydroperoxide.

In U.S. Pat. No. 4,246,203 a hydroperoxide of an aromatic compound is converted to a volatile phenol and a carbonyl compound in a cleavage decomposition reaction. Here a wide range of both solid and liquid cleavage catalysts may be used including acetic acid, sulfur dioxide, sulfur, formic acid, phosphoric acid and fluoroboric acid, although sulfuric acid is preferred.

Silica/alumina gave rather poor yields of phenol and acetone under these conditions.

Lewis acid catalysts were employed in the invention of U.S. Pat. No. 4,267,380, to Austin et al, to decompose cumene hydroperoxide to phenol and acetone, Some Lewis acids were unsatisfactory or, in some cases, found to be catalytically inert. Preferred Lewis acids were tungsten hexafluoride, silicon tetrafluoride, stannous chloride, stannic fluoride, antimony pentachloride, sulfur monochloride and sulfur tetrafluoride.

In U.S. Pat. No. 4,209,465, also to Austin et al, it was found that cumene hydroperoxide could be decomposed to phenol and acetone using an isolable carbonium, tropylium or oxonium salt, such as triphenylcarbonium tetrafluoroborate, as the catalyst.

In another patent to Austin et al, U.S. Pat. No. 4,267,379, cumene hydroperoxide is decomposed to phenol and acetone using boron trifluoride or boron trifluoride complexed with an oxygen-containing polar compound.

In U.S. Pat. No. 4,358,618 there is described a process for decomposing a cumene oxidation product mixture by mixing the product with an acid that lowers the cumene hydroperoxide concentration and converts most of the dimethylphenol carbinol to dicumyl peroxide.

In an article by Augustin Et al, in *Stud. Univ. Babes-Bolyai, Chem.* 1986, 31, 19–23 (see Chem. Abstracts 107:236170j, 1987), "The Life of Synthetic Aluminosilicate Catalysts In The Decomposition Of Cumene Hydroperoxide" was studied.

In U.S. Pat. No. 4,743,573 to Romano there are described catalysts for the selective decomposition of cumene hydroperoxide into phenol and acetone which comprise oxide forms of silicon, aluminum and boron in the form of crystals having a structure of zeolite wherein aluminum and boron replace silicon in the crystalline structure of silica and wherein the crystals are interconnected by oligomeric silica. The phenol selectivity is typically 80.5 to 96% with these catalyts in batch studies, and higher than 98% in continuous synthesis at cumene hydroperoxide conversion levels of 90%.

European patent application No. 203-632-A describes a catalyst for decomposition of cumene hydroperoxide to produce phenol and acetone comprising zeolite crystals containing boron and aluminum bonded with silica. A portion of the silicon atoms in the crystal lattice of silica are replaced by Al and B and the zeolite crystals are bonded to each other by a siliceous bonding agent which allows the catalyst to assume the shape of mechanically stable microspheres.

Carboxylic acid derivatives have also been used to catalyze cumene hydroperoxide decomposition. See *Izv. Akad. Nauk Turkm.* 5512, *Ser. Fiz.—Tekh, Khim, Geol. Nauk* 1987, (2), 108-10 (Russ) and Chem. Abstracts 108:55583w (1988).

Molybdenum, vanadium and titanium catalysts have also been used for the catalytic decomposition of cumyl hydroperoxide to yield mainly phenol and acetone. See Stozhkova, G. A., et al. (Yarosl. Politekh. Inst., Yaroslavl, USSR) *Neftekhimiya* 1987, 27(1), 137–41 (Russ) and Chem. Abstracts 107:197676g (1987).

In the cases where acidic substances are utilized as the catalysts the yields are satisfactory, however many of these acid catalysts required substantial expenditure for production of phenol and acetone, there are disposal problems with spent acids or their salts, and there are difficulties in achieving >99.9% purity phenol required by today's market place due to entrainment or breakthrough of said acids. In addition, by-products such as mesityl oxide, α-methylstyrene, acetophenone and 2-phenyl-2-propanol are produced along with the product and must somehow be removed and processed.

It would be a substantial advance in the art if phenol and acetone could be produced in yields approaching 100% by decomposition over an inexpensive heterogeneous catalyst using mild conditions. A catalyst which worked at high space velocities using mild conditions and yet afforded high selectivities and yields with a smaller percentage of by-products would be particularly advantageous. Furthermore a very active, long life heterogeneous catalyst would also solve the catalyst disposal and acid entrainment problems cited above.

SUMMARY OF THE INVENTION

In accordance with certain of its aspects, the novel method of this invention for continuous cogeneration of phenol and acetone comprises reacting cumene hydroperoxide in the presence of a catalyst from the group consisting of a heteropoly acid supported on an inert support or an ion exchange resin having a sulfonic acid functionality. Particularly effective are heteropoly acids such as tungstophosphoric, molybdophosphoric, tungstosilicic or molybdosilicic acid preferably on an inert, high surface area support, such as titania, using mild conditions.

A particular advantage of the instant invention over the prior art is that it has been discovered in the instant invention that heteropoly acids on titania have properties which allow for distinct improvements over the use of $H_2SO_4$ and $SO_2$. The method of the invention gives essentially quantitative conversion of cumene hydroperoxide under mild conditions with phenol and acetone as the major product fractions. Continuous generation of phenol/acetone in a plug flow reactor at LHSV's of 1–10 have been demonstrated.

DESCRIPTION OF THE INVENTION

Preparation of the product of this invention may be carried out typically by reacting cumene hydroperoxide in the presence of a heterogenous catalyst comprising a heteropoly acid on an inert support or ion exchange resin having a sulfonic acid functionality. The decomposition is carried out continuously and the catalyst preferably comprises a heteropoly acid on an inert, high surface area support.

The reaction can be represented by the following:

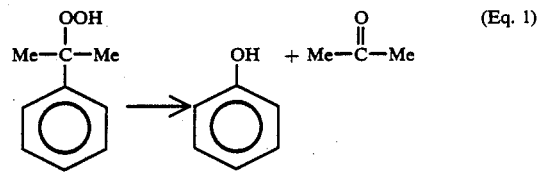
(Eq. 1)

The catalysts used to effect this reaction are preferably heteropoly acids on titania. The catalysts are effective in the form of powders, granules or extrudates.

The heteropoly acids that are catalysts in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

$$PO_4^{3-} + 12WO_4^{2-} + 27H^+ \rightarrow H_3PW_{12}O_{40} + 12H_2O \quad \text{(Eq. 2)}$$

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. No. 3,947,332 (1976)].

TABLE 1

Typical heteropolymolybdate anions

| CONDENSATION RATIOS | | HETERO ATOMS(X) | | CHEMICAL FORMULAS |
|---|---|---|---|---|
| 1:12 | Keggin structure | $P^{5+}, As^{5+}, Si^{4+}, Ge^{4+}$ | | $[X^{n+}Mo_{12}O_{40}]^{-(8-n)}$ |
| | Silverton structure | $Ce^{4+}, Th^{4+}$ | | $[X^{4+}Mo_{12}O_{42}]^{8-}$ |
| 1:11 | Keggin structure (decomposition) | $P^{5+}, As^{5+}, Ge^{4+}, Si^{4+}$ | | $[X^{n+}Mo_{11}O_{39}]^{-(12-n)}$ |
| 2:18 | Dawson structure | $P^{5+}, As^{5+}$ | | $[X_2^{5+}Mo_{18}O_{62}]^{6-}$ |
| 1:9 | Waugh structure | $Mn^{4+}, Ni^{4+}$ | | $[X^{4+}Mo_9O_{32}]^{6-}$ |
| 1:6 | Anderson structure | (A type) | $Te^{6+}, I^{7+}$ | $[X^{n+}Mo_6O_{24}]^{-(12-n)}$ |
| | | (B type) | $Co^{3+}, Al^{3+}, Cr^{3+}$ | $[X^{n+}Mo_6O_{24}H_6]^{-(6-n)}$ |
| 4:12 | | $As^{5+}$ | | $[H_4As_4Mo_{12}O_{52}]^{4-}$ |
| 2:5 | | $P^{5+}$ | | $[P_2Mo_5O_{23}]^{6-}$ |

In the case of conversion of cumene hydroperoxide to phenol/acetone, suitable heterpoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where X=P or SI, M=Mo or W and n is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as their hydrates; they may be employed by themselves, partially or completely dissolved in the cumene hydroperoxide feed, or they may be employed as heterogeneous catalysts bonded to a suitable support.

The support should preferably comprise an inert compound. Compounds which may be employed are those containing elements of Group III and IV of the Periodic Table. Suitable compounds include the oxides of aluminum, silicon, titanium and zironium or combinations thereof, e.g. alumina, silica (silicon dioxide), titania (titanium dioxide) and zirconia, as well as combinations thereof. Also suitable are carbon, ion-exchange resins and carbon-containing supports. Good results were observed using $TiO_2$ as the support.

The inert support may be in the form of powders, pellets, spheres, shapes and extrudates. As will be demonstrated by the examples, the supports are preferably of high purity and high surface area. It has been found in the process of this invention that greater conversion of cumene hydroperoxide is achieved where the surface area of the support is generally $>10$ m$^2$/g.

The reaction may be carried out in either a stirred slurry reactor or in a fixed bed continuous flow reactor. The catalyst concentration should be sufficient to provide the desired catalytic effect.

The weight percent of heteropoly acid to Group III/Group IV support should be such that the concentration of the polyatom (Mo, W, Nb or V) in the formulated catalyst is in the range of 0.1wt % to 30 wt %, although concentrations outside this range may also be employed. Where the heteropoly acid is, for example, 12-molybdophosphoric acid, supported on titania, a suitable quantity of molybdenum is 1-10 wt %. In the preparation of a tungstophosphoric acid-on-titania catalyst, on the other hand, the tungsten content may be 1-30 wt %.

In the second embodiment the ion exchange resins used as catalysts comprise a class of ion exchange resins having a strongly acidic cation exchange. These include the gel type or macroreticular ion exchange resin with sulfonic acid (—$SO_3H$), or substituted sulfonic acid functional groups, wherein the sulfonic acid functional group is bonded directly or indirectly to an organic, preferably polystyrene or styrene-divinylbenzene polymer backbone. Examples of such resins include AMBERLYST ® 15 and XN-1010, AMBERLITE ® IR-118, DOWEX ® 50×2-100 and 5×8-100, XL-383 and -386, plus BIO RAD ® AG50W-X2 and AMBERSEP ® 252H. Another suitable ion exchange resin is Rohm and Haas' B-24 high temperature resin, as well as DuPont's NAFION ® resin, having the perfluoro sulfonic acid functionality. Preferred are the macroporous resins with the styrene-divinylbenzene polymer backbone, sulfonic acid functionality, and 1-20% cross-linking, such as AMBERLYST ® 15 and XN-1010. Said resins should be in the acid (hydrogen) form..

Cumene hydroperoxide decomposition may be conducted batchwise, in a continuous slurry bed reactor, or in a fixed-bed, continuous flow, reactor. For practical reasons a fixed bed process is preferred. In all cases the catalyst concentration should be sufficient to provide the desired catalytic effect.

Cogeneration of phenol and acetone can generally be conducted at temperatures from 20° to 150° C.; the preferred range is 40° to 120° C. The operating pressure may be from zero to 1000 psig, or higher. The preferred pressure range is 100 to 400 psig. Because of the highly exothermic nature (52 kal/mole) of the cumene hydroperoxide decomposition (Eq. 1), temperature control is particularly important, especially in a fixed catalyst process.

Typically, phenol is generated continuously in up to ca. 60 wt % concentration in the crude product liquid effluent, and likewise, acetone may be generated in 40 wt % concentrations. The cumene hydroperoxide should preferably be as pure as possible, but a 60-80% purity is certainly acceptable. Typical impurities in such an "80%" cumene hydroperoxide feed are cumene, 2-phenyl-2-propanol and acetophenone. Said cumene hydroperoxide is generally diluted with inert solvent, or product, prior to being fed to the decomposer. Typical diluents include acetone, or a mix of acetone, cumene and/or phenol.

Generally cumene hydroperoxide conversions are quantitative in continuous unit operations. Phenol yields, based on hydroperoxide charged, are $>99$ mole %. Likewise, acetone yields are also 99 mole % or better.

These yields are achieved at total liquid hourly space velocities (LHSV) of one to 10 under mild conditions. Continuous generation of phenol/acetone in a plug flow reactor at LHSV's of 1-10 have been demonstrated, for example, with AMBERLYST ® XN-1010 resin, and with 12-molybdophosphoric acid-on-titania.

Here LHSV is defined as follows:

$$LHSV = \frac{\text{Weight Of Total Liquid Feed Run Through The Reactor Per Hour}}{\text{Volume of Catalyst In Reactor}}$$

Conversion of cumene hydroperoxide (wt %) is estimated in the following examples using the equation:

$$\frac{\text{Wt \% Conc. of } (C_6H_5C(CH_3)_2OOH) \text{ in Feed} - \text{Wt \% Conc. of Cumene Hydroperoxide in product}}{\text{Wt \% Conc. of Cumene Hydroperoxide in Feed}} \times 100$$

Yields of phenol/acetone ($C_6H_5OH/CH_3COCH_3$, mole %) are estimated from:

$$\frac{\text{Moles of Phenol or Acetone in Product Liquid}}{\text{Moles of Cumene Hydroperoxide in feed}} \times 100$$

The examples which follow illustrate the cogeneration of phenol and acetone from cumene hydroperoxide using heterogenous catalysts, particularly heteropoly acids on a titania support. The examples are only intended as a means of illustration and it should be understood that the invention is not meant to be limited thereby.

EXAMPLE A

This example illustrates the preparation of a typical heteropoly acid-on-titania catalyst.

To a solution of 12-tungstophosphoric acid (40.0 g) in water (150 cc) was added, with stirring, to 125 cc of HSA titania carrier extrudate (from Norton Company, #64467, ⅛" extrudates, surface area Ca. 60 m$^2$/g). The liquid was absorbed into the extrudates, with stirring, for 1-2 hours. The mixture was then rotary evaporated to remove excess liquid and calcined at 150°-350° C. in a stream of nitrogen.

Weight of recovered, white, extrudates: 150.8 g (Sample #5972-83R)
Analyses showed the presence of:
W=17.0%
P=0.6%

EXAMPLE B

This example illustrates the preparation of another typical heteropoly acid catalyst To a solution of 12-molybdophosphoric acid (30.0 g) in water (250 cc) was added, with stirring, a 375 cc of HSA titania carrier extrudate (from Norton Company, #64775, 51 m²/g surface area). The liquid was absorbed into the extrudates, with stirring, for 1-2 hours. The mixture was then rotary evaporated to remove excess liquid and calcined at 150°-350° C. in a stream of nitrogen.

Weight of recovered, yellow, extrudates was 252 g.
Analyses showed the presence of:
Mo=2.8%
P=0.09%

EXAMPLE 1

The data in Example 1 illustrate the quantitative conversion of cumene hydroperoxide to phenol/acetone catalyzed by tungstophosphoric acid on titania catalyst of Example A. Reaction is conducted under mild conditions. Minor by-products include alpha-methylstyrene; cumene, acetophenone and 2-phenylpropanol and are present in the cumene hydroperoxide feed and are apparently remaining to some extent in the mix during peroxide decomposition.

A 250-ml round bottom flask fitted with a condenser, heater, stirrer and feed control, is charged with a mixture of 60.0 g of acetone and 5.0 g of 12-tungstophosphoric acid on titania (5972-83R, 17%W). The mixture is heated to reflux (57° C.) with stirring, and 40.0 g of 80% cumene hydroperoxide solution$^a$ added dropwise at a rate such that the pot temperature did not exceed 80° C. After the peroxide addition was complete, the mixture was heated to reflux for an additional 2 hours.

Upon cooling, the product mix is weighed (104.1 g), and the product liquid (volume 113 ml) neutralized with sodium bicarbonate and analyzed by GLC.

Analysis showed the following composition (wt %):

| | |
|---|---|
| Acetone | 70.9 |
| Phenol | 19.6 |
| Cumene | 6.7 |
| Alpha-methyl styrene | 1.4 |
| 2-phenyl-2-propanol | 0.3 |
| Acetophenone | <0.1 |
| Cumene hydroperoxide | <0.1 |
| $^a$Feed Composition: | |
| Cumene hydroperoxide | 78.5 |
| Cumene | 16.5 |
| 2-phenyl-2-propanol | 4.7 |
| Acetophenone | 0.4 |

Estimated yield of phenol (based on cumyl hydroperoxide charged) is >99 mole %.

EXAMPLES 2-14

Following the procedures of Example 1, the cogeneration of phenol plus acetone has been demonstrated using a series of heteropoly acid catalysts and sulfonic acid resins. The results are summarized in Table 1.

It may be noted that phenol/acetone generation from the same 80% cumene hydroperoxide of Example 1 has been demonstrated using as catalysts:

(a) A variety of heterogeneous heteropoly acids, including tungstophosphoric acid, molybdophosphoric acid, tungstosilicic acid and molybdosilicic acid, each supported on titania (See Examples 1-6).

(b) A variety of different resins containing the sulfonic acid functionality, including Rohm & Haas's AMBERLYST® XN-1010, AMBERLITE® IR-118, AMBERLYST® 15, NAFION® resin and high temperature resin, B-24 also from Rohm & Haas (See Examples 7-11).

It may also be noted from a review of the data in Table I that:

(1) Resins such as DUOLITE® C-467 having the phosphoric acid functionality are not effective for the desired cumene hydroperoxide decomposition reaction to phenol/acetone (See Example 12) under these screening conditions.

(2) Other acidic catalysts such as phosphoric acid-on-titania and boric acid, prepared by methods similar to that of Example A, are far less effective for cumene hydroperoxide conversion to phenol/acetone (Examples 13 and 14).

(3) Both the heteropoly acid and resin-type catalysts, convert much of the 2-phenyl-2-propanol in the cumene hydroperoxide feed (See Example I) into phenol/acetone.

TABLE I

PHENOL/ACETONE FROM CUMENE HYDROPEROXIDE

←Product Composition (Wt %)→

| Ex. 1 | Catalyst | Acetone | Mesityl Oxide | Cumene | α-Methyl Sytrene | Phenol | 2-Phenyl-2-Propanol | Aceto-phenone | Cumene Hydro-peroxide |
|---|---|---|---|---|---|---|---|---|---|
| 1 | W—P/TiO2$^a$ | 70.9 | 0.3 | 6.7 | 1.4 | 19.6 | 0.3 | — | — |
| 2 | Mo—P/TiO2$^b$ | 70.6 | — | 6.9 | 1.8 | 20.0 | 0.3 | — | — |
| 3 | ¼(Mo—P/TiO2) | 69.4 | — | 7.2 | 2.1 | 20.7 | 0.1 | 0.3 | — |
| 4 | ¼(Mo—P/TiO2) | 68.5 | — | 7.6 | 2.0 | 21.3 | 0.2 | 0.3 | — |
| 5 | Mo—Si/TiO2$^c$ | 71.5 | — | 6.8 | — | 19.5 | 0.3 | — | — |
| 6. | W—Si—SiO2$^d$ | 69.0 | 0.1 | 7.3 | 1.7 | 21.0 | 0.1 | 0.3 | — |
| 7. | AMBERLYST® XN-1010$^e$ | 70.5 | 1.5 | 6.7 | 2.1 | 18.3 | 0.2 | 0.3 | — |
| 8. | AMBERLITE® IR-118$^f$ | 69.7 | 0.2 | 7.3 | 1.9 | 19.7 | 0.5 | 0.3 | 0.1 |
| 9. | AMBERLYST® 15 | 67.8 | 1.2 | 7.4 | 2.3 | 20.5 | 0.2 | 0.3 | — |
| 10. | NAFION® Resin | 67.2 | 2.8 | 7.1 | 1.5 | 20.3 | 0.1 | 0.3 | — |
| 11. | Resin B-24$^g$ | 69.8 | — | 6.9 | 2.3 | 19.4 | 0.4 | 0.4 | — |
| 12. | Duolite | 589 | — | 6.7 | — | — | 2.2 | 0.2 | 31.9 |

TABLE I-continued
PHENOL/ACETONE FROM CUMENE HYDROPEROXIDE

| | | ←Product Composition (Wt %)→ | | | | | | |
|---|---|---|---|---|---|---|---|---|
| Ex. 1 | Catalyst | Acetone | Mesityl Oxide | Cumene | α-Methyl Sytrene | Phenol | 2-Phenyl-2-Propanol | Aceto-phenone | Cumene Hydro-peroxide |
| 13. | C-467[h] H$_3$PO$_4$/TiO$_2$ | 63.8 | — | 7.0 | — | 3.6 | 2.2 | 0.2 | 23.2 |
| 14. | H$_3$BO$_3$/TiO$_2$ | 57.9 | — | 6.8 | — | — | 2.4 | 0.2 | 32.7 |

[a]Tungstophorphoric acid on titania, 17.0% W
[b]Molybdophosphoric acid on titania, 2.2% Mo
[c]Molybdosilicic acid on titania, 10.0% Mo
[d]Tungstosilicic acid on titania
[e]AMBERLYST ® XN-1010 from Rohm & Haas
[f]AMBERLITE ® IR-118 from Rohm & Haas
[g]Experimental high temperature resin from Rohm & Haas
[h]Duolite C-467 from Rohm & Haas

EXAMPLES 15-19

To a 150-ml capacity, continuous, plug-flow reactor, fitted with heating, cooling, and feed control, is charged Rohm & Haas AMBERLYST® XN-1010 resin. The resin is pretreated with acetone at 60° C. and then fed a mixture of acetone (2100 g) and 80% cumene hydroperoxide (900 g) at various flow rates (150-600 g/hr, LHSV-1-4), reactor bed temperatures (60°-80° C.) and pressures (300-600 psi). The results are summarized in Table II.

The data show almost quantitative conversion of cumyl hydroperoxide over the full range of conditions evaluated in this work. Due to the exothermic nature of hydroperoxide decomposition, the temperature of the reactor bed varied over its length considerably; the observed range is given in Col. 3 of Table II.

From these data it may be noted that:

(a) The estimated yield of phenol, based on cumyl hydroperoxide charged, is: 98 mole %.

(b) A substantial portion of the 2-phenyl-2-propanol in the feed is also converted to product.

(c) There is a significant quantity of mesityl oxide by-product formed with this catalyst.

(d) Cumene hydroperoxide conversion is essentially quantitative at the lower operating temperature (60° C.).

12-tungstosilicic acid and silica (united catalysts, 4 mm×4 mm) and having a 16.0 wt % tungsten loading.

An analysis of the crude product solution shows the presence of (wt %):

| | |
|---|---|
| Acetone | 64.2 |
| Phenol | 22.6 |
| Cumene | 8.3 |
| α-methylstyrene | 3.1 |
| 2-phenyl-2-propanol | 0.1 |
| Acetophenone | 0.3 |
| Cumene Hydroperoxide | <0.1 |

Estimated yield of phenol (based on cumyl hydroperoxide charged) is >99 mole %.

EXAMPLE 21

This example illustrates the generation of phenol/acetone in continuous unit equipment using the sulfonic acid resin catalyst, AMBERLYST® XN-1010 and a cumene hydroperoxide feed stream diluted with acetone/cumene/phenol mix.

Employing the reactor and procedures of Example 15, 150 cc of AMBERLYST® XN-1010 was pretreated with acetone (150 cc/hr) at 60° C., then fed a mixture of "80%" cumene hydroperoxide (900 g, composition as in Example 1) diluted with acetone/-

TABLE II
PHENOL/ACETONE FROM CUMENE HYDROPEROXIDE

| | | | | | | ←Product Composition→ | | | | | | |
|---|---|---|---|---|---|---|---|---|---|---|---|---|
| Ex. | Operating Temp. (°C.) | Bed Temp. (°C.)[a] | Press. (psi) | Rate (g/hr) | Sample | Acetone | Mesityl Oxide | Cumene | Phenol | α-methyl Styrene | Aceto-Phenone | 2-Phenyl 2-Propanol | Cumene Hydro peroxide |
| 15 | 60 | 57-80 | 300 | 150 | 3 | 72.4 | 4.1 | 5.4 | 15.0 | 1.5 | 0.3 | 0.2 | — |
|  |  | 56-74 | — | — | 5 | 74.9 | 3.4 | 5.0 | 14.1 | 1.4 | 0.3 | 0.1 | — |
| 16 | 60 | 55-84 | 300 | 300 | 1 | 69.5 | 3.6 | 6.2 | 17.7 | 1.8 | 0.4 | 0.2 | — |
|  |  | 56-79 | — | — | 5 | 69.1 | 3.4 | 6.3 | 18.0 | 1.8 | 0.4 | 0.2 | — |
| 17 | 60 | 56-78 | 300 | 600 | 9 | 69.6 | 2.3 | 6.3 | 16.8 | 1.7 | 0.4 | 0.3 | 2.3 |
|  |  | 54-75 | — | — | 13 | 69.8 | 1.9 | 6.2 | 15.5 | 1.5 | 0.3 | 0.4 | 3.9 |
| 18 | 80 | 80-105 | 300 | 150 | 15 | 62.9 | 7.1 | 6.7 | 18.0 | 2.5 | 0.9 | 0.2 | 0.2 |
|  |  | 80-100 | — | — | 18 | 72.3 | 5.2 | 5.1 | 13.5 | 1.8 | 0.6 | 0.2 | 0.3 |
| 19 | 80 | 80-92 | 600 | 150 | 21 | 72.7 | 4.8 | 5.1 | 13.1 | 1.7 | 0.5 | 0.2 | 0.8 |
|  |  | 80-90 | — | — | 24 | 71.7 | 4.6 | 54 | 13.5 | 1.8 | 0.5 | 0.2 | 1.4 |

[a]Catalyst: AMBERLYST ® XN-1010

EXAMPLE 20

Following the procedures of Example 1, a sample (40.0 g) of 80% cumene hydroperoxide solution in acetone (60.0 g) is converted to phenol/acetone in the presence of 12-tungstosilicic acid-on-silica catalyst, prepared according to the procedure of Example A using cumene/phenol (6.4:1.4:9.2 weight ratio, 2100 g) at a feed rate of 150 cc/hr. Operating temperatures and pressures were 60° C. and 300 psi. Samples of crude liquid product effluent were collected and analyzed. Results are summarized in Table III.

It may be noted that in typical samples, e.g. Sample #18:

Estimated phenol yield=>99 mole %

Estimated acetone yield = 88 mole %
Cumene hydroperoxide conversion was essentially complete.

molybdophosphoric acid-on-titania catalyst of Example B and a cumene hydroperoxide feed stream diluted with acetone/cumene/phenol mix.

TABLE III

PHENOL/ACETONE FROM CUMENE HYDROPEROXIDE

←CRUDE PRODUCT COMPOSITION (WT %)→

| Ex. | Catalyst | Temp. (°C.) | (g/hr) | Sample | Acetone | Mesityl Oxide | Cumene | Phenol | Methyl Styrene | Aceto-Phenone | 2-Phenyl 2-Propanol | Cumene Hydro-Peroxide | 4-Cumyl Phenol |
|---|---|---|---|---|---|---|---|---|---|---|---|---|---|
| 21 | XN-1010[a] | 60 | 150 | 1 | 30.7 | 2.3 | 13.4 | 51.1 | — | 0.2 | — | — | 1.7 |
|  |  |  |  | 3 | 28.0 | 2.4 | 13.8 | 53.5 | — | 0.2 | — | — | 1.5 |
|  |  |  |  | 4 | 30.7 | 2.2 | 13.3 | 51.6 | — | 0.2 | — | — | 1.6 |
|  |  |  |  | 5 | 27.6 | 2.3 | 13.8 | 53.7 | 0.1 | 0.2 | 0.1 | — | 1.9 |
|  |  |  |  | 9 | 31.1 | 1.8 | 13.4 | 51.1 | 0.2 | 0.2 | — | — | 1.9 |
|  |  |  |  | 10 | 31.4 | 1.8 | 13.4 | 51.0 | 0.2 | 0.2 | — | — | 1.6 |
|  |  |  |  | 11 | 31.7 | 1.6 | 13.9 | 50.8 | 0.2 | 0.2 | — | — | 1.2 |
|  |  |  |  | 12 | 31.4 | 1.6 | 13.9 | 50.9 | 50.9 | 0.2 | — | 0.2 | 1.4 |
|  |  |  |  | 13 | 24.7 | 1.7 | 14.7 | 56.5 | 0.3 | — | 0.2 | — | 1.3 |
|  |  |  |  | 14 | 24.9 | 1.5 | 14.7 | 56.5 | 0.3 | 0.2 | 0.1 | — | 1.5 |
|  |  |  |  | 18 | 31.6 | 1.2 | 13.9 | 51.2 | 0.4 | — | 0.2 | — | 1.1 |
|  |  |  |  | 20 | 31.9 | 1.1 | 13.9 | 51.1 | 0.4 | — | 0.2 | — | 1.1 |
| FEED: |  |  |  |  | 24.1 |  | 13.3 | 36.7 |  | 0.1 | 1.5 | 24.3 |  |

[a]Rohm & Haas AMBERLYST ® XN-1010

EXAMPLE 22

Following the procedure of Example 21, a fresh batch of AMBERLYST® XN-1010 was tested for phenol/acetone production at higher liquid feed rates (0.9–3.3 lb/hr., LHSV's of 3–10) at a reactor temperature of 44° C. Results are summarized in Table IV.

It may be noted that with this AMBERLYST® XN-1010 catlayst, the conversion of cumene hydroperoxide is incomplete at the highest feed rates and mesityl oxide is a consistent by-product in each of these runs. Consequently in Sample #18, at LHSV's of 10:
Estimated phenol yield = 55 Mole %
Estimated acetone yield = 53 mole %
Cumene hydroperoxide conversion = 56%

Employing the reactor and procedures of Example 15, 150 cc of 12-molybdophosphoric acid-on-titania were pretreated with acetone (150 cc/hr) at 60° C., then fed a mixture of "80%" cumene hydroperoxide (900 g, composition as in Example 1) diluted with acetone/cumene/phenol (6.4:2.4:9.1 weight ratio 0.2100 g) at a feed rate of 150 cc/hr. Operating temperatures and pressures were 60° C. and 300 psi. Samples of crude liquid product effluent were collected and analyzed. Results are summarized in Table V.

It may be noted that in the 4th day of the run, Sample #14 shows:
Estimated Phenol Yield = 94 mole %
Estimated Acetone Yield = 99 mole %
Cumene hydroperoxide conversion was essentially complete.

TABLE IV

PHENOL/PRODUCT COMPOSITION (WT %)

←Product Composition (Wt %)→

| Ex. | Catalyst | Temp. (°C.) | Feed Rate (lb/hr) | Sample | Acetone | Mesityl Oxide | Cumene | Phenol | Methyl Styrene | Aceto Phenone | 2-Phenyl 2-Propanol | Cumene Hydroperoxide | 4-Cumyl Phenol |
|---|---|---|---|---|---|---|---|---|---|---|---|---|---|
| 22 | XN-1010[a] | 44 | 0.99 | 1 | 31.2 | 0.9 | 14.9 | 50.5 | 0.2 | 0.2 | — | — | 1.9 |
|  |  |  |  | 4 | 32.5 | 0.7 | 14.6 | 50.0 | 0.3 | 0.2 | — | — | 1.5 |
|  |  | 44 | 1.65 | 8 | 32.9 | 0.6 | 14.5 | 49.9 | 0.4 | 0.2 | 0.1 | — | 1.2 |
|  |  |  |  | 10 | 33.0 | 0.4 | 14.6 | 50.0 | 0.4 | 0.2 | 0.1 | — | 1.0 |
|  |  |  |  | 12 | 31.7 | 0.4 | 14.7 | 51.2 | 0.4 | 0.2 | 0.2 | — | 0.9 |
|  |  | 44 | 3.3 | 13 | 31.3 | 0.1 | 15.1 | 47.5 | 0.3 | 0.2 | 0.7 | 4.3 | 0.3 |
|  |  |  |  | 17 | 29.6 | 0.1 | 14.9 | 44.0 | 0.3 | 0.1 | 0.8 | 9.8 | 0.3 |
|  |  |  |  | 18 | 29.2 | 0.1 | 14.9 | 43.7 | 0.3 | 0.1 | 0.9 | 10.4 | 0.3 |
| FEED: |  |  |  |  | 24.5 |  | 14.6 | 35.8 |  | 0.1 | 1.4 | 23.6 |  |

[a]AMBERLYST ® 1010 Resin

EXAMPLE 23

This example illustrates the generation of phenol/acetone in continuous unit equipment using the 12-

TABLE V

PHENOL/ACETONE FROM CUMENE HYDROPEROXIDE

←Product Composition (Wt %)→

| Ex. | Catalyst | Temp. (°C.) | (g/hr) | Sample | Acetone | Mesityl Oxide | Cumene | Phenol | Methyl Styrene | Aceto-Phenone | 2-Phenyl 2-Propanol | Cumene Hydro-Peroxide | 4-Cumyl Phenol | Day |
|---|---|---|---|---|---|---|---|---|---|---|---|---|---|---|
| 23 | MoP/TiO$_2$[a] | 60 | 150 | 1 | 26.6 | — | 15.0 | 56.4 | 0.3 | — | 0.2 | — | 0.9 | 1 |
|  |  |  |  | 2 | 33.3 | — | 14.2 | 50.5 | 0.4 | — | 0.2 | — | 0.9 |  |
|  |  |  |  | 3 | 33.3 | — | 14.2 | 50.6 | 0.5 | — | 0.2 | — | 0.6 | 2 |
|  |  |  |  | 5 | 33.3 | — | 14.2 | 50.5 | 0.6 | 0.2 | — | — | 0.6 |  |
|  |  |  |  | 7 | 33.3 | — | 14.2 | 50.5 | 0.7 | — | 0.2 | — | 0.5 | 3 |

TABLE V-continued

| | | | | | | PHENOL/ACETONE FROM CUMENE HYDROPEROXIDE | | | | | | | |
|---|---|---|---|---|---|---|---|---|---|---|---|---|---|
| | | | | | | ←Product Composition (Wt %)→ | | | | | | | |
| Ex. | Cat-alyst | Temp. (°C.) | (g/hr) | Sample | Ace-tone | Mesityl Oxide | Cumene | Phenol | Methyl Styrene | Aceto-Phenone | 2-Phenyl 2-Pro-panol | Cumene Hydro-Peroxide | 4-Cumyl Phenol | Day |
| | | | | 9 | 33.3 | — | 14.1 | 50.7 | 0.7 | 0.2 | 0.1 | — | 0.5[b] | |
| | | | | 12 | 33.3 | — | 14.0 | 50.7 | 0.8 | 0.2 | 0.1 | — | 0.4 | 4 |
| | | | | 14 | 33.3 | — | 14.2 | 50.6 | 0.8 | 0.2 | 0.1 | — | 0.3 | |
| | | | | 15 | 33.3 | — | 14.1 | 50.6 | 0.9 | 0.2 | 0.1 | — | 0.3[c] | 5 |
| | | | | 16 | 33.4 | — | 14.0 | 50.6 | 0.9 | 0.2 | 0.1 | — | 0.4[d] | |
| FEED: | | | | | 24.4 | | 14.0 | 36.9 | | 0.1 | 1.4 | 23.1 | | |

[a]Molybdophosphoric Acid-On-Titania, Sample From Example B

EXAMPLE 24

Following the procedures of Example 23, a fresh batch of 12-molybdophosphoric acid-on-titania was tested for phenol/acetone production at higher liquid feed rates (0.9–33 lb/hr, LHSV's of 3–10). Results are summarized in Table VI.

It may be noted that good results are obtained with this catalyst even at LHSV's of 10, and there is no evidence for methyl oxide by-product formation. Illustrative are the results for #14, where:
Estimated Phenol Yield=>95 mole %
Estimated Acetone Yield=88 mole %
Cumene Hydroperoxide Conversion=97%

TABLE VI

| | | | | | | PHENOL/ACETONE FROM CUMENE HYDROPEROXIDE | | | | | | | |
|---|---|---|---|---|---|---|---|---|---|---|---|---|---|
| | | | | | | ←Product Composition (Wt %)→ | | | | | | | |
| Ex. | Catalyst | Temp. (°C.) | Feed Rate (lb/hr) | Sam-ple | Ace-tone | Mesityl Oxide | Cumene | Phenol | methyl Styrene | Aceto-Phenone | 2-Phenyl 2-Pro-panol | Cumene Hydro-Peroxide | 4-Cumyl Phenol |
| 24 | Mo—P/TiO₂[A] | 60 | 0.99 | 1 | 33.5 | — | 14.1 | 50.5 | 0.9 | — | 0.2 | 0.1 | 0.2 |
| | | | | 2 | 33.6 | — | 14.2 | 50.3 | 1.1 | — | 0.2 | — | 0.1 |
| | | | | 4 | 33.6 | — | 14.2 | 50.2 | 1.3 | — | 0.2 | — | 0.1 |
| | | | 1.65 | 5 | 33.5 | — | 14.1 | 50.2 | 1.5 | — | 0.2 | — | — |
| | | | | 8 | 33.7 | — | 14.1 | 50.3 | 1.3 | — | 0.2 | — | — |
| | | | | 9 | 33.7 | — | 14.1 | 50.1 | 1.5 | — | 0.2 | — | — |
| | | | 3.3 | 12 | 33.0 | — | 14.2 | 50.2 | 1.4 | 0.2 | 0.2 | 0.5 | — |
| | | | | 14 | 33.0 | — | 14.2 | 50.2 | 1.4 | 0.2 | 0.2 | 0.7 | — |
| | | | | 15 | 33.3 | — | 14.3 | 49.2 | 1.9 | 0.2 | 0.2 | 0.7 | — |
| FEED | | | | | 25.4 | — | 14.5 | 35.5 | | 1.6 | | 22.9 | |

[A]12-Molybdophosphoric Acid-On-Titania, Sample Example B

What is claimed is:

1. In a method for cosynthesis of phenol and acetone by acid-catalyzed decomposition over a catalyst, the improvement comprising reacting cumene hydroperoxide over a heterogeneous catalyst consisting essentially of a heteropoly acid on an inert support at a temperature of about 20° to 150° C. and a pressure of from zero to 1000 psig.

2. The method of claim 1 wherein the heteropoly acids have the Keggin structure, $H_{8-n}[XM_{12}O_{40}]$, where X=P or Si, M=Mo or W and n is an integer which is 4 or 5.

3. The method of claim 1 wherein the heterogeneous catalyst is a heterpoly acid from the class of acids formed by the condensation of two more inorganic oxyacids.

4. The method of claim 1 wherein the heteropoly acid catalysts are selected from the group consisting of 12-tungstophosphoric acid, 12-molybdophosphoric acid, tungstosilicic acid and 12-molybdosilicic acid.

5. The method of claim 3 wherein the inert support is an oxide selected from the group consisting of titanium dioxide, alumina and silica.

6. The method of claim 3 wherein the wt % concentration of polyatom in the formulated catalyst is in the range of 0.1 to 30 wt %.

7. The method of claim 4 wherein said inert support has a surface area of $>10$ m²/g.

8. The method of claim 1 wherein the heteropoly acid is 12-molybdophosphoric acid, the support is titanium dioxide and the molybdenum content in the formulated catalyst is 1 to 10 wt %.

9. The method of claim 1 wherein the heteropoly acid is 12-tungstophosphoric acid, the support is titanium dioxide and the tungsten content in the formulated catalyst is in the range of 1 to 30 wt %.

10. The method of claim 1 wherein the heteropoly acid is 12-tungstosilicic acid and the inert support is silica.

11. The method of claim 1 wherein phenol/acetone are produced continuously and the feed liquid hourly space velocity (LHSV) is between 1 and 10.

12. The method of claim 1 wherein the temperature is between 40° and 120° C.

13. The method of claim 1 wherein the operating pressure is from 100 psig and 400 psig.

14. The method of claim 1 wherein the cumene hydroperoxide feed has a purity of at least 60%.

15. The method of claim 1 wherein the cumene hydroperoxide feed is diluted with a solvent from the group consisting of acetone or a mix of acetone, cumene and/or phenol.

* * * * *